United States Patent
Hanes et al.

(10) Patent No.: US 9,227,902 B2
(45) Date of Patent: Jan. 5, 2016

(54) COMPOSITIONS FOR CARBOXYLIC ACID PRODUCTION AND METHODS FOR MAKING AND USING SAME

(71) Applicant: PRETIUM VENTURES AA, LLC, Houston, TX (US)

(72) Inventors: Ronnie M. Hanes, Union Grove, AL (US); Peter P. Hanik, Houston, TX (US); James A. Hinnenkamp, Houston, TX (US)

(73) Assignee: Pretium Ventures AA, LLC, Houston, TX (US)

(*) Notice: Subject to any disclaimer, the term of this patent is extended or adjusted under 35 U.S.C. 154(b) by 0 days.

(21) Appl. No.: 14/245,047

(22) Filed: Apr. 4, 2014

(65) Prior Publication Data

US 2014/0350296 A1    Nov. 27, 2014

Related U.S. Application Data

(62) Division of application No. 12/494,098, filed on Jun. 29, 2009, now abandoned.

(60) Provisional application No. 61/133,398, filed on Jun. 28, 2008.

(51) Int. Cl.
| | |
|---|---|
| *C07C 51/12* | (2006.01) |
| *B01J 31/20* | (2006.01) |
| *C07C 51/50* | (2006.01) |
| *B01J 8/00* | (2006.01) |

(52) U.S. Cl.
CPC . *C07C 51/12* (2013.01); *B01J 8/00* (2013.01); *B01J 31/20* (2013.01); *C07C 51/50* (2013.01); *B01J 2219/00006* (2013.01); *B01J 2231/321* (2013.01); *B01J 2531/822* (2013.01); *B01J 2531/827* (2013.01); *C07C 2523/46* (2013.01)

(58) Field of Classification Search
None
See application file for complete search history.

(56) References Cited

FOREIGN PATENT DOCUMENTS

WO        01/49644    *  7/2001

* cited by examiner

*Primary Examiner* — Karl J Puttlitz
(74) *Attorney, Agent, or Firm* — Robert W Strozier

(57) ABSTRACT

An alcohol such as methanol is reacted with carbon monoxide in a liquid reaction medium including a catalyst, an alkyl iodide such as methyl iodide, alkyl acetate such as methyl acetate in specified proportions, an additive, and an effective amount of water, where the additive increases an ionic character of the hydrogen iodide bond and the effective amount of water is sufficient to facilitate carboxylic acid release after carbonylation at the catalyst and to reduce anhydride formation. The present reaction system not only provides an acid product at water levels considerable below levels currently used, but also provides unexpected reaction rates and unexpected high catalyst stability.

18 Claims, 4 Drawing Sheets

Initial Rh (I) Concentration (%) in Media and Rh(I) Concentration after 20 Minutes of Reaction

COMPOSITIONS FOR CARBOXYLIC ACID PRODUCTION AND METHODS FOR MAKING AND USING SAME

RELATED APPLICATIONS

This application is a divisional application of U.S. patent application Ser. No. 12/494,098, filed Jun. 29, 2009, which claims priority to and the benefit of U.S. Provisional Patent Application Ser. No. 61/133,398, filed Jun. 28, 2008.

BACKGROUND OF THE INVENTION

1. Field of the Invention

Embodiments of the present invention relate to a composition for carboxylic acid production and methods for making and using same.

More particularly, embodiments of the present invention relate to a composition for carboxylic acid production and methods for making and using same, where the composition includes a metal catalyst, carbon monoxide, an alkanol, an iodine source, an additive providing hydrogen bonding to HI present in the reaction media, and optionally added water.

2. Description of the Related Art

Production of acetic acid via methanol carbonylation is an industrial process used on a global basis to produce billions of pounds of glacial acetic acid. The process as currently practiced commercially operates under relatively mild conditions with high selectivity for utilization of methanol and carbon monoxide raw materials.

A large body of literature pertaining to this process exists and a review of this literature indicates several key operating parameters that must be considered for efficient process operation. One of these parameters concerns maintaining a low concentration of water in the reactor. This requirement is obvious; glacial acetic acid is marketed with a water concentration in the parts per million range. Thus, reactor water above ppm levels must be removed, requiring energy—the more water, the higher the energy requirement.

Those skilled in the art are familiar with the original literature by Monsanto (see, e.g., U.S. Pat. No. 3,769,329, inventor of the basic modern process) and a reading of this literature indicates a second parameter concerning catalyst stability. Catalyst stability is adversely affected by lower reactor water concentrations. Moreover, increasing water increases by-product formation due to such reactions as the water gas shift reaction, which is directly proportional to the reactor water concentration.

Another problem with the current processes is that catalyst stability and activity is lower than desired even with high reactor water concentrations. The literature indicates that oxidative addition of hydrogen iodide to the active rhodium species is the first step in a series of reactions leading to both the undesired water gas shift reaction and to rhodium precipitation. See, e.g., N. Hallinan and J. Hinnenkamp, Rhodium Catalyzed Methanol Carbonylation: New Low Water Technology, Proceedings of the Organic Reactions Catalysis Society, 2000. The reference disclosed one can inhibit the addition of hydrogen iodide to the rhodium species through the interaction of HI with a weak base such as a tertiary phosphine oxide. The reference further disclosed that if too strong a base is used, the hydrogen iodide intermediate is removed from the iodide cycle such that methyl iodide is not regenerated from methyl acetate and the reaction rate drops significantly and even stops. Thus, selection of an additive with a base strength within a very narrow range is effective in maintaining the rhodium in the desired active and stable form independent of reactor water concentration.

Thus, there is a need in the art for an improved carboxylic acid preparation process. The new processes and catalyst compositions provide a means to provide improved catalyst stability, reduced energy consumption, and reduced by-product formation. Because the catalyst metals used in this process are expensive (e.g., Rh, Ir, Pd, etc.), improving catalyst stability and simplifying acetic acid recovery can decrease metal loss and reduce catalyst regeneration.

SUMMARY OF THE INVENTION

Embodiments of the present invention relate to liquid reaction media for carbonylation of alcohols to carboxylic acids, where the media include a catalyst, an alcohol (ROH) or alcohol equivalents such as an alkyl acetate (AcOR), a source of iodide to form an alkyl iodide (RI), an effective amount of an additive, and optionally an effective amount of added water in the presence of carbon monoxide, where the media converts the alcohol to a carboxylic acid having one more carbon atom, the effective amount of the additive is sufficient to increase an ionic character of the hydrogen iodide bond produced during the carbonylation reaction, to reduce added water below levels currently used or eliminate added water and to improve catalyst stability and where the effective amount of added water is sufficient to facilitate carboxylic acid formation after carbonylation of the alcohol at the catalyst and to reduce anhydride formation.

Embodiments of the present invention relate to systems for producing carboxylic acids, including a reaction subsystem including at least one reactor vessel charged with a liquid reaction media of this invention, reactant sources, feed lines from the reactant sources to the reactor, a separation subsystem for separating the product carboxylic acid from the media and a recycle subsystem of recycling the media to the reaction subsystem.

Embodiments of the present invention relate to methods for producing carboxylic acids, including charging a reactor vessel with a liquid reaction media of this invention. Once the media is charged, supplying carbon monoxide to the reaction vessel. After reaction or on a continuous or semi-continuous basis, removing the media or a portion thereof. After removing the media or a portion thereof, separating the low boiling components including the carboxylic acid and recycling the high boiling components back to the reactor vessel. After separating the low boiling components, purifying the carboxylic acid and returning other low boiling components to the reactor vessel.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
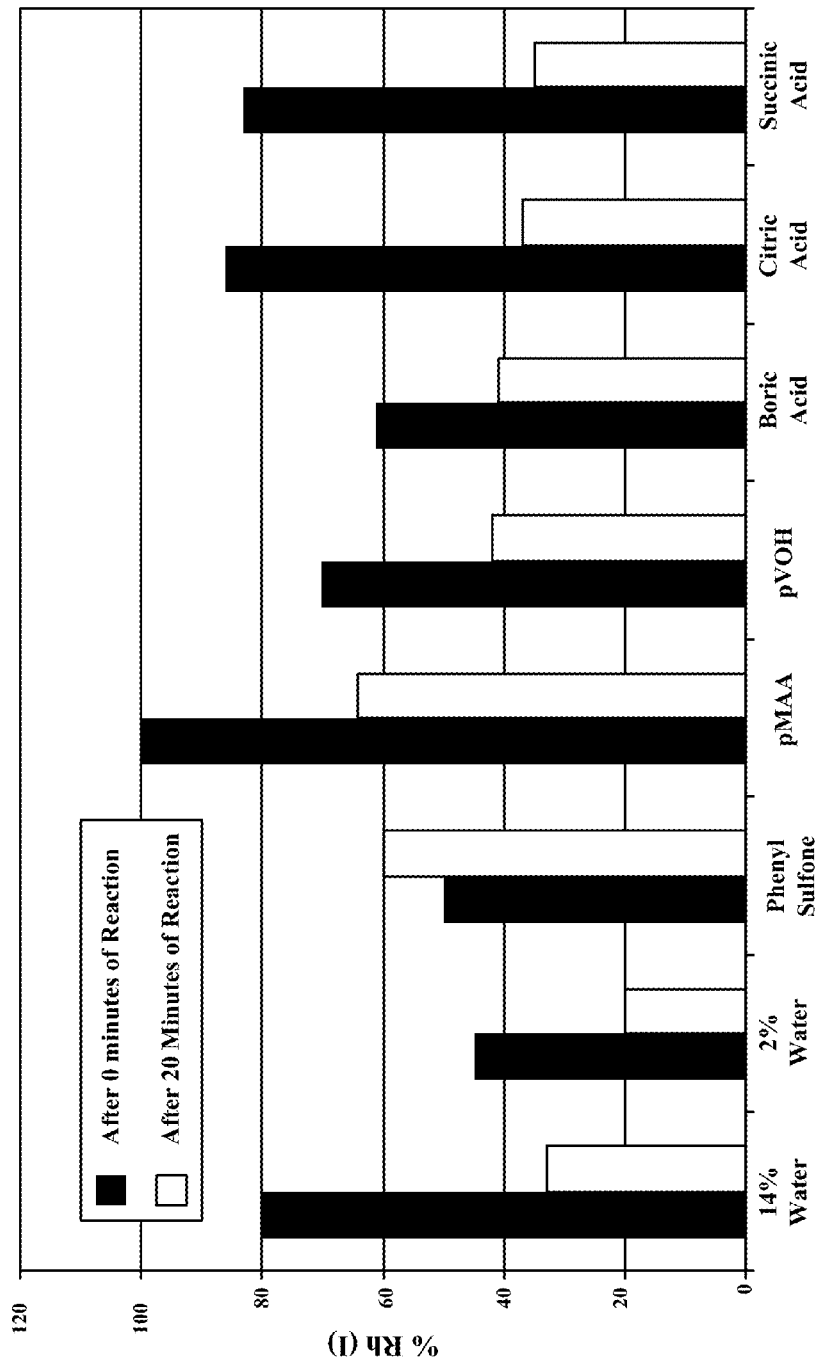
FIG. 1 depicts a graph of initial Rh(I) concentrations and Rh(I) concentration after 20 minutes of reaction for various additives of this invention relative to a 14 wt. % water and a 2 wt. % water controls.
Figure 2:
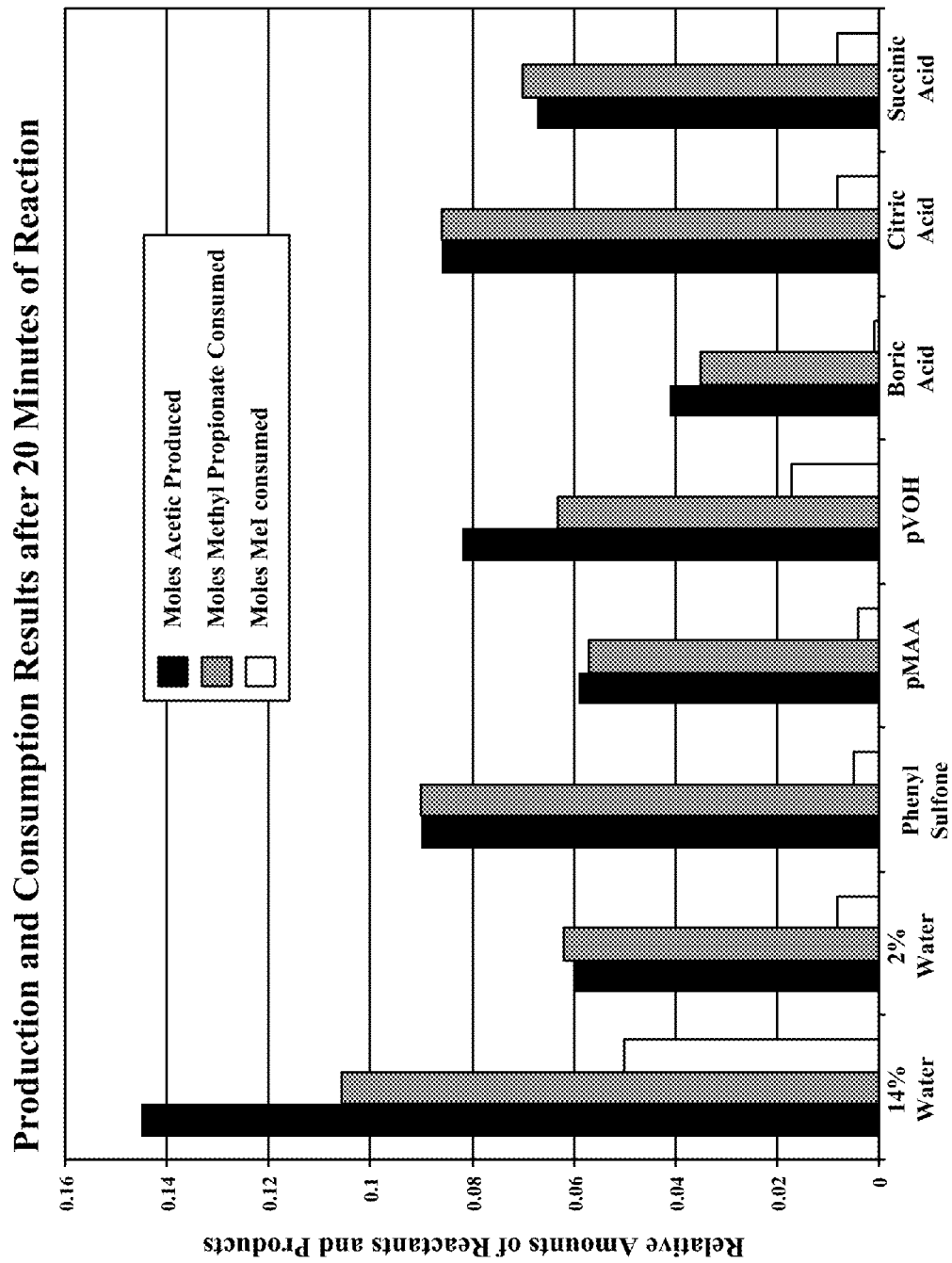
FIG. 2 depicts a graph of moles of acetic acid produced, moles of methyl propanoate consumed, and moles of methyl iodide consumed for various additives of this invention relative to a 14 wt. % water and a 2 wt. % water controls.
Figure 3:
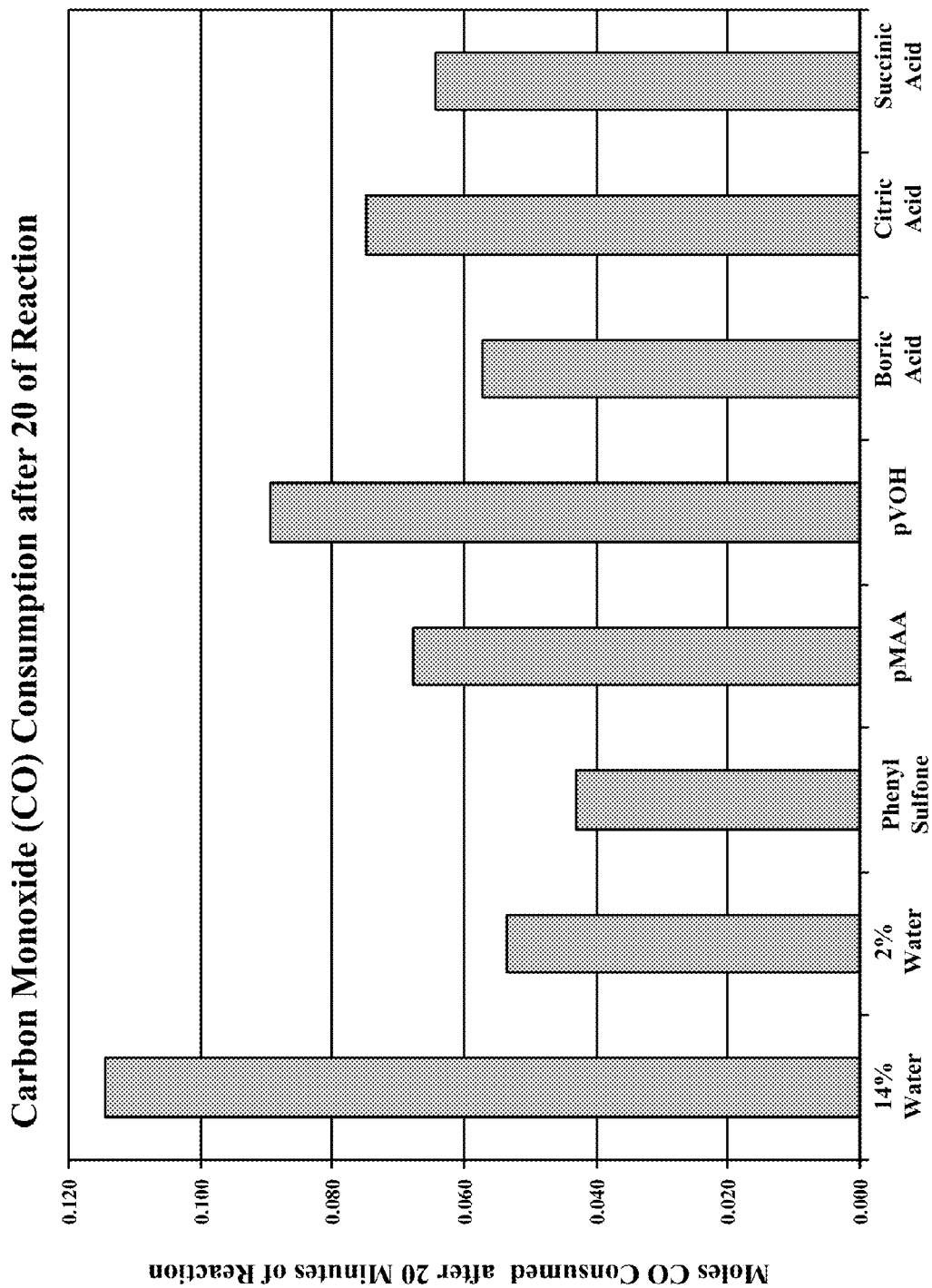
FIG. 3 depicts a graph of moles of carbon monoxide consumed for various additives of this invention relative to a 14 wt. % water and a 2 wt. % water controls.
Figure 4:
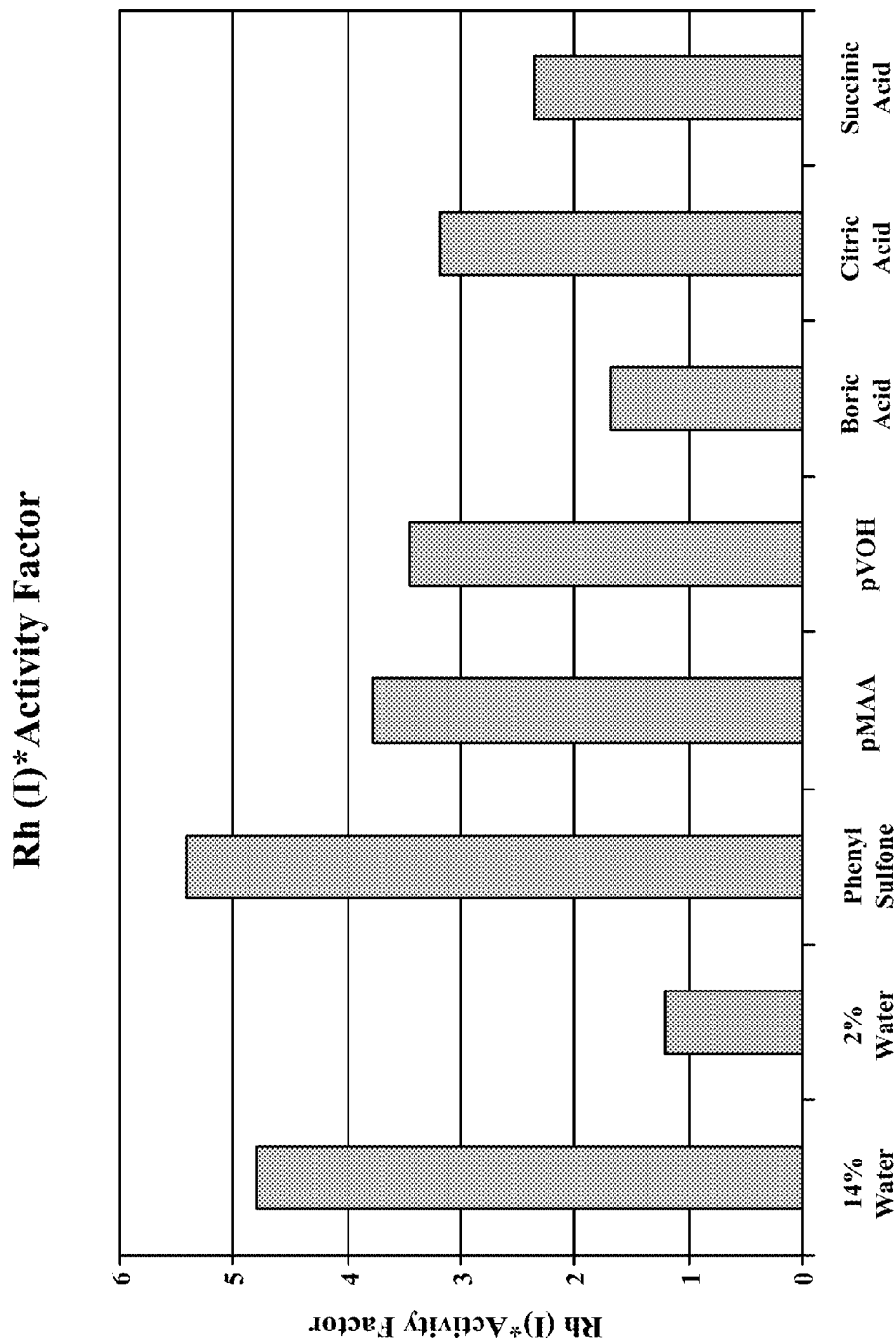
FIG. 4 depicts a graph of moles of Rh(I)* activity factor for 14 wt. % water, 2 wt. % water, phenyl sulfone, pMAA, pVOH, Boric Acid, Citric Acid, and Succinic Acid.

The inventors have found that new catalytic compositions and methods for using these compositions to prepare carboxylic acids via carbonylation of an alcohol or alcohol equivalent can be formulated and implemented. The inventors have found that catalyst activity and stability can be improved through the addition of one additive or a plurality of additives, which increase an ionic character of the bond of hydrogen iodide (HI) formed during the carbonylation reaction. The literature supports a mechanism for producing a carboxylic acid (RCOOH) such as acetic acid (AcOH). The mechanism is thought to include an oxidative addition of an alkyl iodide (RI) such as methyl iodide (MeI) to a metal catalytic species such as a rhodium and/or iridium and/or palladium catalytic species to form a pre-carbonylation intermediate. The mechanism is also thought to support a similar mechanism for by-product production and catalyst precipitation that starts with an oxidative addition of hydrogen iodide (HI) to the metal catalytic species instead of the alkyl iodide. The addition of HI is thought to be the first step in the water gas shift reaction (a by-product reaction) and the first step in a reaction that leads to catalyst precipitation. It is known that hydrogen iodide (HI) has the unique capability of exhibiting either covalent bonding or ionic bonding, while the methyl(alkyl) iodide (MeI (RI)) possesses only covalent bond character. While not meaning to be bound to any particular theory, the inventors have inferred from the action of the weak base in the Hallinan and Hinnenkamp reference discussed above, that the oxidative addition of HI to the metal catalytic species occurs when HI is in a covalently bonded state, the HI bond is covalent, not ionic. Moreover, the inventors have further inferred that the reaction between methyl (alkyl) acetate and HI to regenerate the methyl(alkyl)iodide occurs when hydrogen iodide is in an ionically bonded state, the HI bond is ionic, not covalent. This latter reaction, the regeneration of MeI, is necessary for the reaction to continue.

The inventors have also found that by adding one additive or a plurality of additives to active media, an amount of HI in its covalently bonded state can be reduced, while increasing an amount of HI in its ionically bonded state. The term "active media" means the liquid reaction media that carbonylates an alkanol equivalent (an acetate), via its iodide, to a carboxylic acid having one additional carbon atom. In certain embodiments, the amount of HI in its covalently bonded state can be substantially eliminated resulting in substantially all of the HI being in its ionically bonded state. The inventors have found that these additives are capable of reducing the amount of covalently bonded HI to substantially eliminating the amount of covalently bonded HI. The additives can be used to optimize an amount of ionically bonded HI. In certain embodiments, the additives can be used to maximize the amount of ionically bonded HI in the active media. By maintaining the HI entirely or substantially entirely in its ionically bonded state, by-product production and catalyst precipitation and/or deactivation through oxidation addition of HI to the metal catalytic species can be minimized and the rate of methyl (alkyl)iodide regeneration can be increased increasing its steady state concentration. The inventors further believe that these observations explain the rate and stability dependence of the active media on water observed in the original process, because water will hydrogen bond with hydrogen iodide increasing an ionic character of the HI bond. The term "substantially" as used here means that at least 85% of the HI present in the active media is in its ionically bonded state. In other embodiments, the term "substantially" means that at least 90% of the HI present in the active media is in its ionically bonded state. In other embodiments, the term "substantially" means that at least 95% of the HI present in the active media is in its ionically bonded state. In other embodiments, the term "substantially" means that at least 99% of the HI present in the active media is in its ionically bonded state.

The inventors have applied these inferences to construct novel active media to increase catalyst activity and stability, while allowing added reactor water to be reduced and/or minimized to that needed for the reaction to proceed or to that cyclically produced and consumed in the reaction, one water molecule produced to form the acetate and one water molecule consumed to form the carboxylic acid from the carbonylation intermediate, Cat-CO-Me. The novel active media includes the addition of stabilizing agents adapted to interact with HI to increase its ionic bond character increasing the amount of ionically bonded HI, reducing the amount of covalently bonded HI, reducing by-product formation and reducing catalyst precipitation.

In the production of acetic acid from methanol carbonylation, methanol is fed to the reactor vessel where it immediately reacts with acetic acid to form methyl acetate and water. Methyl acetate, thus, formed then reacts with HI to form methyl iodide and acetic acid. The addition of methyl iodide to the active catalyst is the rate limiting step in the carbonylation reaction. Therefore, as water is liberated in the formation of methyl acetate from methanol and acetic acid, it is immediately consumed in the liberation of acetic acid from the carbonylated methylated catalyst (RhCOMe). The steady state water concentration maintained in the reaction is used to facilitate conversion of acetic anhydride back to acetic acid. The present invention is to add additives to reduce added water to a concentration less than 2 wt. %. Embodiments of this invention, the water concentration is less than 1 wt. %. Embodiments of this invention, the water concentration is less than 0.5 wt. %.

Broadly, embodiments of the present invention relate to active media including additives capable of increasing the ionic bond character of HI in the active media.

Embodiments of the present invention also relate to active media including a low vapor pressure additive or additives, where the additive or additives are present in an amount or concentration sufficient to maintain all or substantially all of the HI in its ionically bonded state. These additives provide catalyst activity and stability, while allowing reactor water concentration to be significantly reduced.

Embodiments of the present invention relate to active media including a low vapor pressure, ionic liquid or a plurality of ionic liquids, where the ionic liquids are present in an amount or concentration sufficient to maintain all or substantially all of the HI in its ionically bonded state. These additives provide catalyst activity and stability, while allowing reactor water concentration to be significantly reduced.

An additional benefit of employing the novel concepts detailed in this invention would be the possible simplification of the production process. If a stable, active catalyst is provided that permits a lower water concentration, potentially even minimizing water to that needed to release the carboxylated MeI as AcOH using low volatility additive under reaction conditions, then the reaction can be carried out in a manner similar to a fixed bed catalyst reactor. That is, the homogeneous catalyst and other reaction components are contained in a reactor vessel from which only product vapor streams are removed. In the current process, liquid streams are removed from the reactor in order to remove the acetic acid produced. With a stable catalyst and low volatility components and water minimized to acetic acid release, reactor conditions can be selected such that the acetic acid can be removed from the reactor as a vapor stream at a production rate of acetic acid under the reaction conditions. This would eliminate the flash vessel and associated recycle equipment. Because the flash vessel is a zone of low carbon monoxide concentration, which destabilizes the rhodium catalyst, removal of this vessel would enhance catalyst stability by removing a low carbon monoxide pressure zone. Moreover, because the flash vessel and associated equipment is constructed of exotic alloys due to the corrosive nature of the process, a significant capital savings would be realized by eliminating this equipment.

Although the kinetic rate constants for the iridium-catalyzed methanol carbonylation processes are different in some steps, the overall reaction mechanism is viewed to be very similar for both rhodium-based and iridium-based processes. Thus, it would be expected that application of the teachings of this invention would have benefits in both the rhodium-based and iridium-based processes for the production of acetic acid, though only the rhodium-based system has been experimentally addressed here. The application also envision the use of palladium-based catalyst systems or mixed catalyst system.

Suitable Reagents and Reagent Ranges

The present invention can be practiced with the ingredients and ranges set forth in Table 1, which lists reagents and additives.

reaction is carried [out] in the absence of any solvent or diluent other than those required to introduce reactants or catalyst components into the reactor." U.S. Pat. No. 5,817,869 at Col. 7, ll. 36-48. This disclosure teaches away from the use of sulfones and the other compounds set forth above designed to increase the ionic bond character of the HI bond, thereby increasing catalyst stability by reducing HI induced catalyst deactivation.

Additives

Suitable additives capable of increasing the ionic bond character of HI include, without limitation: (1) polyols ($R^1(OH)_n$), compounds including two or more hydroxy groups, where in n is an integer having a value between 2 and the maximum number of hydroxy groups that can be accommodated based on the number of carbon atoms in the $R^1$ group, (2) poly carboxylic acids ($R^2(COOH)_n$), compounds including two or more carboxylic acid groups, where in n is an integer having a value between 2 and the maximum number of carboxylic groups that can be accommodated based on the number of carbon atoms in the $R^2$ group, (3) sulfones ($R^3SO_2R^4$), (4) oligomers, co-oligomers, polymers and co-polymers including at least one hydroxy containing monomer (poly(OH)), (5) oligomers, co-oligomers, polymers and co-polymers including at least one carboxylic acid containing monomer (poly(COOH)), (6) oligomers, co-oligomers, polymers and co-polymers including at least one sulfone containing monomer (poly($SO_2$)), (7) other compounds capable of increasing the ionic character of the HI bond, and (8) mixtures thereof. In certain embodiments, the additive(s) have a boiling point or vaporization temperature at least 10° C. above a temperature of the product carboxylic acid. Such high boiling additives would remain in a reactor/flash tank section of the process simplifying the distillation section of the process.

TABLE 1

Reagent Table

| Component | Exemplary Examples | | Ranges |
|---|---|---|---|
| Catalyst Metals | rhodium (Rh), iridium (Ir), palladium (Pd), or mixtures or combinations thereof | | 100 ppm-1200 ppm |
| Alcohol Source | alkyl acetate (AcOR) | | N/A |
| Iodide Source | alkyl iodide (RI) or alkyl acetic (AcOR)/HI | | N/A |
| Solvating Additives | carboxylic acids, sulfones, polyols, other weak acids, mixtures thereof, etc. | | 0.1M-3M |
| | Carboxylic Acids | di-carboxylic acids, tri-carboxylic acids, tetra-carboxylic acids, poly-carboxylic acids, oliogomers and polymers containing carboxylic acid monomers such as acrylic acid, methacrylic acid, maleic anhydride, etc., cooligomers and copolymers containing a carboxylic acid monomer, etc. and mixtures thereof | |
| | Sulfones | dialkyl sulfones ($RSO_2R'$), diaryl sulfones ($ASO_2A'$), alky, aryl sulfones ($RSO_2A$), sulfone oligomers, polysulfones, sulfone cooligomers and copolymers, etc. and mixtures thereof | |
| | Polyols | compounds including two or more hydroxy group ($R(OH)_n$), vinyl alcohol oliogmers and polymers, vinyl alcohol cooligomers and copolymers, etc. | |
| | Weak Acids | boric acid, boronic acids, etc. | |
| Hydroxide Donors | water | added water | 0 wt. % to wt. % |

Although sulfolane, a cyclic alkenyl sulfone (five membered ring), has been used as a solvent, which U.S. Pat. No. 5,817,869 disclosed as being inert in the reaction media. "The term 'inert' as used herein means that the solvent or diluent does not interfere with the reaction to any significant extent." U.S. Pat. No. 5,817,869 at Col. 7, ll. 28-30. "Generally, the The $R^1$, $R^2$, $R^3$, and $R^4$ groups in the above formulas are generally carbyl group including from about 1 to about 20 carbon atoms. The groups can be alkyl, aryl, aralkyl, alkaryl, or combinations thereof.

As employed herein, the alkyl groups, singly or in combination with other groups, include between 1 to 20 carbon atoms and may be linear, branched, or cyclic. Non-limiting exemplary examples including methyl, ethyl, propyl, isopropyl, butyl, isobutyl, t-butyl, amyl, pentyl, hexyl, octyl, cyclopropyl, cyclobutyl, cyclopentyl, cyclohexyl, and the like. In certain embodiments, the alkyl groups include between 1 to 8 carbon atoms.

As employed herein, the aryl groups are aromatic ring compounds including between from 6 to 18 carbon atoms. Non-limiting exemplary examples including phenyl, benzyl, tolyl, xylyl, α-naphthyl, β-naphthyl, and the like. In certain embodiments, the aryl group is phenyl.

As employed herein, the aralkyl groups, singly or in combination with other groups, contain up to 16 carbon atoms with each aryl group containing from 6 to 10 carbon atoms and each alkyl group containing up to 6 carbon atoms which may be in the normal or branched configuration. Preferably, each aryl group contains 6 carbon atoms and each alkyl group contains 1 to 3 carbon atoms.

As employed herein, the alkaryl groups, singly or in combination with other groups, contain up to 16 carbon atoms with each alkyl group containing up to 8 carbon atoms which may be in the normal or branched configuration, and each aryl group containing from 6 to 10 carbon atoms. Preferably, each alkyl group contains 6 carbon atoms.

As indicated herein each $R^1$, $R^2$, $R^3$, and $R^4$ group may be substituted or unsubstituted. When $R^1$, $R^2$, $R^3$, and/or $R^4$ are substituted, it is typically substituted with an alkyl group as defined herein above. $R^1$, $R^2$, $R^3$, and/or $R^4$ may also be substituted with other substituents such as halogen, hydroxy, nitro, amino and the like.

In certain embodiments, from about 0.2 to about 3M (or about 0.3 wt. % to about 4 wt. %) of one additive or a plurality of additives are present in the liquid reaction medium. In other embodiments, from about 0.4 to about 1.5M (or about 0.6 wt. % to about 2 wt. %) of one additive or a plurality of additives are present in the liquid reaction medium.

Other Additives

Suitable secondary additives can include, without limitations, alkali iodides such as lithium iodide (LiI), sodium iodide (NaI), potassium iodide (KI), or the like or mixtures thereof (see, e.g., U.S. Pat. Nos. 5,214,203; 5,391,821; 5,003,104; 5,001,259; 5,026,908; 5,144,068; 5,281,751 and 5,416,237), pentavalent Group VA oxide of the formula: $R_3M=O$, where M is an element from Group VA of the Periodic Table of Elements, such as N, P, As, Sb or Bi; and each R is independently a substituted or unsubstituted alkyl, aryl, aralkyl or alkaryl wherein any of which substituents of the carbon chains may be straight or branched or both (see, e.g., U.S. Pat. No. 5,817,869), alkali and alkaline metal fluorides (LiF, NaF, KF, $MgF_2$, $CaF_2$, etc.) or other fluoride salts, metal sulfates, metal sulfites, or mixtures or combinations thereof.

The pentavalent Group VA oxide is introduced into the carbonylation system in an amount such that its concentration relative to rhodium is greater than about 60:1. The practice of the invention further comprises introducing water to the carbonylation system at an amount of from about 0 wt. % to about 3 wt. % (which corresponds to a molarity of water of from about 0 M to about 7.5M) based on the total amount of the carbonylation system, inclusive of the additives and other additives such as pentavalent Group VA oxide(s). In other embodiments, the concentration of water is from about 0.5 wt. to about 2 wt. %. In other embodiments, the concentration is about 1 wt. % to about 2 wt. %. It should be recognized that the water concentration can be higher for those system including novel HI solvating additives of this invention.

Solvents

Suitable solvents for use in the present invention include, without limitation, alkyl carboxylic acids such as acetic acid, propanoic acid, butanoic acid, or other linear carboxylic acids. Other solvents well known the art can also be used such as dioxane, sulfolane, or other such solvents.

Catalysts

Suitable catalyst for use in the present invention include, without limitation, rhodium based catalysts, iridium based catalysts, palladium based catalysts, or mixtures thereof. In certain embodiments, the catalyst is a rhodium based catalyst. In other embodiments, the catalyst is an iridium based catalyst.

Non-limiting exemplary examples of rhodium-based catalysts for use in the present invention include those known and used in the prior art for carbonylation purposes. In certain embodiments, the rhodium-based catalysts are those used in the prior art especially for the production of acetic acid via carbonylation.

The rhodium-based catalysts of this invention may be introduced into the reaction zone as a suitable compound of rhodium or of rhodium metal. Among the materials which may be charged into the reaction zone in this regard are, without limitation, rhodium metal, rhodium salts, rhodium oxides, rhodium acetates, organo-rhodium compounds, coordination compounds of rhodium, and the like or mixtures or combinations thereof.

Non-limiting specific examples of rhodium-containing compounds that can serve as the rhodium source for the rhodium based catalysts of this invention include $RhCl_3$; $RhBr_3$; $RhI_3$; $RhCl_3.3H_2O$; $RhBr_3.3H_2O$; $RhI_3.3H_2O$; $Rh_2(CO)_4Cl_2$; $Rh_2(CO)_4Br_2$; $Rh_2(CO)_4I_2$; $Rh_2(CO)_8$; $Rh(CH_3CO_2)_2$; $Rh(CH_3CO_2)_3$; $Rh[(C_6H_5)_3P]_2(CO)I$; $Rh[(C_6H_5P)]_2(CO)Cl$; Rh metal; $Rh(NO_3)_3$; $Rh(SnCl_3)[(C_6H_5)_3P]_2$; $RhCl(CO)[(C_6H_5)_3As]_2$; $RhI(CO)[(C_6H_5)_3Sb]_2$; $[Y][Rh(CO)_2X_2]$, where X is $Cl^-$, $Br^-$ or $I^-$; and Y is a cation selected from the group consisting of positive ions from Group IA of the Periodic Table of Elements, such as H, Li, Na, K, or Y is a quaternary ion of N, As or P; $Rh[(C_6H_5)_3P]_2(CO)Br$; $Rh[(n-C_4H_9)_3P]_2(CO)Br$; $Rh[(n-C_4H_9)_3P]_2(CO)I$; $RhBr[(C_6H_5)_3P]_3$; $RhI[(C_6H_5)_3P]_3$; $RhCl[(C_6H_5)_3P]_3$; $RhCl[(C_6H_5)_3P]_3H_2$; $[(C_6H_5)_3P]_3Rh(CO)H$; $Rh_2O_3$; $[Rh(C_3H_4)_2Cl]_2$; $K_4Rh_2Cl_2(SnCl_2)_4$; $K_4Rh_2Br_2(SnBr_3)_4$; $[H][Rh(CO)_2I_2]$; $K_4Rh_2I_2(SnI_2)_4$, and the like and mixtures or combinations thereof.

In certain embodiments, rhodium-containing compounds that can serve as the rhodium source for the rhodium based catalysts of this invention include $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H][Rh(CO)_2I_2]$ or mixtures or combinations thereof. In other embodiments, rhodium-containing compounds that can serve as the rhodium source for the rhodium based catalysts of this invention include $[H][Rh(CO)_2I_2]$, $Rh(CH_3CO_2)_2$, $Rh(CH_3CO_2)_3$ or mixtures or combinations thereof.

In practice, the rhodium concentration can vary over a wide range, although it is recognized that enough metal must be present to achieve reasonable carbonylation reaction rates; excess metal on the other hand may on occasion result in undesired by-product formation. In certain embodiments, the rhodium concentration is from about 200 to about 1200 ppm (about $2\times10^{-3}$ to about $13\times10^{-3}$ M). In other embodiments, the rhodium concentration is from about 400 to about 1000 ppm (about $4\times10^{-3}$ to about $10\times10^{-3}$ M). The amount of rhodium used is not a critical feature and higher concentrations are acceptable, subject to economic considerations.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO).sub.4I_2]^-H^+$, $[Ir(CO)_2]^-H^+$, $[Ir(CO).sup.2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, $Ir_2O_3$, $IrO_2$, Ir(acac)$(CO)_2$, $Ir(acac)_3$, $Ir(Ac)_3$, $[Ir_3O(OAc)_6(H_2O)_3][OAc]$, and $H_2[IrCl_6]$. In certain embodiment, the iridium compounds are selected from the group consisting of acetates, oxalates, acetoacetates, the like, and mixtures thereof. In certain embodiments, the iridium compounds are acetates.

In certain embodiments, the iridium catalyst is used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. In other embodiments, the co-catalysts are selected from the group consisting of ruthenium compounds and osmium compounds. In other embodiments, the co-catalysts are ruthenium compounds. In other embodiments, the co-catalysts are chloride-free such as acetates.

As indicated above, the carbonylation system 1 includes catalytic component, e.g., a rhodium-containing component, as described above, and a liquid reaction medium which generally comprises methyl acetate, methyl iodide and acetic acid and at least one additive, which improves catalytic component stability and reduces added water concentration. In certain embodiments, the added water can be reduced substantially to zero.

In the practice of the invention, water is deliberately introduced in selected amounts into the carbonylation system. The concentration of water present in carbonylation system to which the instant invention relates is from about 0.5 wt. % to about 12 wt. % (about 0.03 to about 7.5 M) based on total weight of the carbonylation system inclusive of all additives. In certain embodiments, the concentration of water present in the carbonylation system is from about 1 to about 3 wt. % (about 0.65 to about 7M); most preferably about 4 to about 9 wt. % water is present.

In accordance with the present invention, the ratio of water to rhodium employed in the present is from about 4000:1 to about 200:1. In certain embodiment, the ratio of water to rhodium employed in the present invention is from about 1750:1 to about 270:1.

Another component of the liquid reaction medium aspect of the carbonylation system to which the instant invention pertains is methyl acetate, which can be charged into the reactor or can be formed in-situ in an amount of from about 0.5 to about 10 wt. % based on the total weight of the liquid reaction medium. The foregoing wt. % range of methyl acetate corresponds to a methyl acetate molarity of from about 0.07 to about 1.4 M. More preferably, the concentration of methyl acetate employed in the process of the present invention is from about 1 to about 8 wt. % (about 0.14 to about 1.1 M).

The corresponding ratio of methyl acetate to rhodium employed in the present invention is from about 700:1 to about 5:1. In other embodiments, the ratio of methyl acetate to rhodium is from about 275:1 to 14:1.

A third component of the subject liquid reaction medium is methyl iodide (MeI), which can be added directly to or can be formed in-situ by using HI. In certain embodiments, the concentration of MeI employed in the instant invention is from about 0.6 to about 36 wt. % (0.05 to about 3 M). In certain embodiments, the concentration of MeI employed in the instant invention is from about 3.6 to about 24 wt. % (about 0.3 to about 2.0M). When HI is employed, it is generally present in a concentration of from about 0.6 to about 23 wt. % (0.05 to about 2.0 M). In certain embodiments, the concentration of HI is from about 2.3 to about 11.6 wt. % (0.2 to about 1.0 M).

The fourth component of the liquid reaction medium is acetic acid (HOAc), which is typically present in the reactor in an amount of from about 20 to about 80 wt. %. The corresponding molarity range being from about 3 to about 12 M. In certain embodiments, the amount of acetic acid that is charged into the reactor is from about 35 to about 65 wt. % (about 5 to about 10 M).

Hydrogen may also be fed into the reactor to increase the overall rate of the carbonylation process. In this embodiment, improved carbonylation efficiency can be obtained when the addition of hydrogen to the reactor maintains a concentration of from about 0.1 to about 5 mole % $H_2$, based on the total number of moles of CO in the reactor. In certain embodiments, hydrogen addition is sufficient to maintain a concentration of from about 0.5 to about 3 mole % $H_2$ in the reactor. Hydrogen may be added to the reactor either as a separate stream or together with carbon monoxide; make-up amounts can be introduced in the same manner, as needed, to maintain the hydrogen concentration at the levels defined hereinabove.

The carbonylation process of the present invention, which does not evince any induction time for carbonylation, can be carried out either in a batch or continuous mode. When operating in a continuous mode, the reaction system hardware usually comprises (a) a liquid phase carbonylation reactor, (b) a so-called "flasher", and (c) a methyl iodide-acetic acid splitter column. Other reaction zones or distillation columns may be present. Such hardware and the operation thereof are well known in the art. When operating in a continuous mode, the carbonylation reactor is typically a stirred autoclave within, which the concentration of the reactants are maintained automatically at a constant level. The present invention also contemplates with low volatility additives and minimum water, a continuous reactor system that does not include a separate flasher, but where a crude product stream is removed as a gas, where the distillation subsystem removes MeI and water for recycling to the reaction.

The carbonylation processes to which the instant invention relates is, for either mode, typically conducted under a pressure of from about 200 to about 1200 psig. In certain embodiments, the carbonylation is conducted under a pressure of about 300 to about 600 psig.

The carbonylation processes to which the present invention relates is typically carried out at a temperature of from about 160° C. to about 220° C. In certain embodiments, carbonylation is carried out at a temperature of from about 170° C. to about 200° C.

In practice, carbonylation reaction time varies, depending upon reaction parameters, reactor size and charge, and the individual components employed.

Experiments of the Invention

Acetic Acid Experimental Procedures

These details are intended for a 300 cc stirred autoclave of Hasteloy, Zirconium or similar corrosion resistant material. Amounts should be adjusted if a different reactor volume is used. The reactor head should be equipped with attachments for cooling coils, thermocouples and dip tubes for sampling and additions under pressure. A means for feeding CO to the reactor from a high pressure reservoir via a regulator should be provided. The reservoir should have a pressure transducer to monitor pressure drop versus time as a means to measure carbonylation rate. Alternately, the CO reservoir could be placed on a scale and CO consumption monitored by weight change The set up used is a 250 cc reservoir pressurized to between about 1200 and about 1600 psi. A larger reservoir at about 1000 psi could also be used if a compressor is not available.

Reaction components, minus the catalyst, should be charged to the reactor according to the experimental table and the reactor assembled per manufacturer directions. The reactor is then leak tested with nitrogen and purged with carbon monoxide. At this point the reactor is pressurized with CO to 100 psig and heated to 186° C. with agitation. The reaction is initiated by injection of a rhodium-containing solution to the reactor contents, adjusting reactor pressure to 400 psig and adjusting the temperature to 186° C. These conditions are maintained for one hour.

At appropriate time intervals as specified (15-20 minutes), samples are removed from the reactor for FTIR and GC analysis. FTIR analysis of the liquid will measure Rh (I) peaks at 1990 and 2060 $cm^{-1}$ and a Rh (III) peak at 2090 $cm^{-1}$ using a liquid cell. Analysis of the liquid will quantify acetic acid, methyl acetate and methyl iodide. At the end of the reaction, the reactor headspace gas should be sampled and analyzed for carbon dioxide and hydrogen to measure the water gas shift reaction.

The active rhodium compound is $[H][Rh(CO)_2I_2]$. This compound is generated in situ immediately after injection of a rhodium acetate pre-catalyst solution. Rhodium acetate is readily soluble in acetic acid containing 10% water. The solution is stable in air at room temperature such that sufficient solution can be prepared for a full week of experimentation. The rhodium concentration should be high enough to provide 500 ppm rhodium in the reactor from the injected solution. For 150 cc of 500 ppm Rh reactor solution with 20 cc rhodium solution injected this would require 3750 ppm rhodium in the stock solution. For 5 runs the basic recipe for the rhodium stock solution is to dissolve 1.164 grams rhodium acetate into 110 mL acetic or propionic acid containing 10% water. Rhodium acetate solid (CAS #42204-14-8) is available from Alfa Aesar (catalog number-43004).

Preparation of Rhodium Stock Solution

A 25 cc round bottom flask fitted with magnetic stirrer and septum closure was purged with carbon monoxide. To this flask was added 0.0235 grams dichloro tetracarbonyl rhodium (I) (CAS #14523-22-9), 20 mL of glacial acetic acid, 0.4 gram of water and 1 drop of hydriodic acid (55-57%). The solution was stirred at room temperature and sparged for 10 minutes with carbon monoxide via a two needle arrangement through the septum. An FTIR spectrum was taken after 10 minutes to confirm the formation of diiodo dicarbonyl rhodium (I) by observation of peaks at 1990 and 2060 $cm^{-1}$.

Rhodium (I) Stability Experiments

To a series of glass vials was added stabilizing compounds in the amounts listed in the table below. To each vial in turn was added 2 drops of an 8:1 solution of acetic acid and hydriodic acid. To each vial was then added 0.5 mL of rhodium stock solution prepared as indicated above. The solution was sparged at room temperature for 6 minutes and a sample was removed for immediate FTIR analysis to measure Rh(I)Rh(III) ratio.

TABLE 2

Additive Amount and Rh(I) to Rh(III) Ratio

| Experiment | Additive | Amount (g) | Rh(I)/Rh(III) |
|---|---|---|---|
| A | potassium sulfite ($Na_2SO_3$) | 0.082 | 4.8 |
| B | poly vinyl alcohol (pVA) | 0.144 | 4.5 |
| C | tetrabutyl ammonium iodide (t-$Bu_4$NI) | 0.111 | 1.3 |
| D | trimethyl phosphate ($Me_3PO$) | 0.037 | 1.3 |
| E | diethylene glycol dibutyl ether | 0.107 | 1 |
| F | potassium sulfate ($KSO_4$) | 0.098 | 1 |
| G | poly methacrylic acid (pMAA) | 0.023 | 0.9 |
| H | potassium iodide (KI) | 0.117 | 0.4 |
| I | 14% water | 0.59 | 0 |
| J | 2% water | NA | 0 |
| K | trifluoroacetic acid (TFA) | 0.277 | 0 |
| L | p-toluene sulfonic acid (TSA) | 0.138 | 0 |

To a series of experiments conducted in a 300 cc stirred reactor outfitted as described above were added the hydrogen-bonding additives as shown in Table 3.

TABLE 3

Reactor Inputs

| Run | Solvent | Amount (mL) | MeI (g) | AcOMe or Propionate | Additive | Amount (g) | Added Water (g) | Rh SS‡ (mL) |
|---|---|---|---|---|---|---|---|---|
| 1 | Propionic | 98.4 | 10.6 | 9.25 | 14% water control | 0 | 17.6 | 20 |
| 2 | Propionic | 115 | 10.6 | 9.25 | 2% water control | 0 | 1 | 20 |
| 3 | Propionic | 115 | 10.6 | 9.25 | φ$SO_2$φ‡ | 12 | 1 | 20 |
| 4 | Propionic | 115 | 10.6 | 9.25 | pMAA | 6 | 1 | 20 |
| 5 | Propionic | 115 | 10.6 | 9.25 | PVOH | 12 | 1 | 20 |
| 6 | Propionic | 115 | 10.6 | 9.25 | Boric Acid | 6 | 1 | 20 |
| 7 | Propionic | 115 | 10.6 | 9.25 | Citric Acid | 6 | 1 | 20 |
| 8 | Propionic | 115 | 10.6 | 9.25 | Succinic Acid | 6 | 1 | 20 |

† Rhodium stock solution of dichloro tetracarbonyl rhodium (I)
‡ diphenyl sulfone The reaction was then conducted at 400 psig with carbon monoxide make-up to maintain pressure and at a temperature of 186° C. FTIR (Fourier Transform Infra Red spectrometry) was used to determine Rh(I) and Rh(III) concentrations, while gas chromatography was used to analyze and characterize all gas and liquid components of the reaction media. Analysis of this series of experiments are tabulated in Table 4.

TABLE 4

Results of Analysis of This Series of Experiments

| Additive | % Rh(I) 0 mins | % Rh(I) | Moles AcOH Produced | Moles AcOMe Consumed | Moles MeI Consumed 20 mins | Grams CO Consumed | Moles CO Consumed | % H$_2$ (WGS) |
|---|---|---|---|---|---|---|---|---|
| 14% Water | 80 | 33 | 0.145 | 0.1055 | 0.05 | 3.2 | 0.114 | 56.0 |
| 2% Water | | | | | | | | |
| No Additive | 45 | 20 | 0.060 | 0.062 | 0.008 | 1.5 | 0.054 | 16.6 |
| Phenyl Sulfone | 50 | 60 | 0.090 | 0.090 | 0.005 | 1.2 | 0.043 | 1.80 |
| Sodium Fluoride | 86 | 84 | 0.060 | 0.004 | 0.060 | 1.5 | 0.054 | 0.50 |
| pMAA†† | 100 | 64 | 0.059 | 0.057 | 0.004 | 1.9 | 0.068 | 15.3 |
| pVOH‡ | 70 | 42 | 0.082 | 0.063 | 0.017 | 2.5 | 0.089 | 0.90 |
| Boric Acid | 61 | 41 | 0.041 | 0.035 | 0.001 | 1.6 | 0.057 | 18.3 |
| Citric Acid | 86 | 37 | 0.086 | 0.086 | 0.008 | 2.1 | 0.075 | 3.90 |
| Succinic Acid | 83 | 35 | 0.067 | 0.070 | 0.008 | 1.8 | 0.064 | 13.5 |

††pMAA is polymethareylic acid
‡pVOH is polyvinylalcohol

The above data shows that phenyl sulfone, pMAA, pVOH, boric acid, citric acid, and succinic acid are effective additives for the production of acetic acid from methanol as the amount of acetic acid (AcOH) produced is nearly identical to the amount of methyl acetate (AcOMe) consumed, while maintaining the amount of methyl iodide (MeI) substantially constant, only 0.004 moles of MeI was consumed during the reaction, where substantially constant means that the amount of MeI consumed is less than about 0.02 moles.

The following table tabulates the Rh(I) active factor for the examples of Table 4.

TABLE 5

Amounts of Rh Active Factor Present in the Reactions

| Additive | Moles Rh*AA† | % Rh (I)‡ | Acetic Acid Produced |
|---|---|---|---|
| 14% Water | 4.785 | 33 | 0.145 |
| 2% Water | 1.2 | 20 | 0.06 |
| Phenyl Sulfone | 5.4 | 60 | 0.09 |
| pMAA | 3.776 | 64 | 0.059 |
| pVOH | 3.444 | 42 | 0.082 |
| Boric Acid | 1.681 | 41 | 0.041 |
| Citric Acid | 3.182 | 37 | 0.086 |
| Succinic Acid | 2.345 | 35 | 0.067 |

†Rhodium Active Factor
‡20 minutes

The data show that all of additives showed improved results relative to 2 wt. % added water, and all increased % Rh(I) by at least a factor of 2 relative to the examples with 2 wt. % added water. Surprisingly, all but boric acid showed results approaching the value of the 14 wt. % added water example, but having only 2 wt. % added water. The data clearly indicate the surprising and unexpected results that these additive, alone or in combination, are effective for their intended purpose in the carbonylation of alkyl alcohols into carboxylic acids having on additional carbon atom, such as the carbonylation of methanol to acetic acid.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for producing carboxylic acids comprising:
charging a reactor vessel with a liquid reaction media comprising:
a metal-containing catalyst,
an alcohol (ROH) forming a corresponding alkyl acetate (AcOR) upon addition to the reaction media,
an alkyl iodide (RI),
one or a plurality of hydrogen iodide (HI) solvating additives selected from the group consisting of sulfones ($R^3SO_2R^4$), oligomers, co-oligomers, polymers and co-polymers including at least one sulfone containing monomer (poly($SO_2$)), and mixtures thereof,
an effective amount of added water of less than 2 wt. %, and
supplying carbon monoxide to the reaction vessel to convert the alcohol (ROH) and/or the alkyl actetate (AcOR) into a carboxylic acid (RCOOH) having one more carbon atom;
removing the media or a portion thereof;
separating the low boiling components including the carboxylic acid (RCOOH) to form a crude carboxylic acid product,
recycling high boiling components back to the reactor vessel;
separating low boiling components from the crude acid product to form a purified carboxylic acid product, and
returning other low boiling components to the reactor vessel,
where the catalyst converts the alcohol into a carboxylic acid having one more carbon atom, the solvating additive increases an ionic character of the hydrogen iodide bond of hydrogen iodide formed during carbonylation reducing the effective amount of added water to a concentration at or below 4 wt. % and improves catalyst stability and where the effective amount of water is sufficient to facilitate the release of carboxylic acid after carbonylation of the alcohol/alkyl acetate and to reduce anhydride formation, where the R group a linear alkyl group having between 1 and 6 carbon atoms, the $R^3$ and $R^4$ groups are carbyl group including from about 1 to about 20 carbon atoms, and where the $R^3$ and $R^4$ groups may be substituted with substituents including halogen atoms, hydroxyl groups, nitro groups, or amino groups.

2. The method of claim 1, wherein in the charging step, the solvating additive has a boiling point or vaporization temperature at least 10° C. above a temperature of the product carboxylic acid.

3. The method of claim 1, wherein in the charging step, the solvating additive comprises sulfones ($R^3SO_2R^4$) and mixtures thereof.

4. The method of claim 1, wherein in the charging step, the solvating additive comprises oligomers, co-oligomers, polymers and co-polymers including at least one sulfone containing monomer (poly($SO_2$)), and mixtures thereof.

5. The method of claim 1, wherein in the charging step, the metal-containing catalyst is present in an amount sufficient to achieve a desired carbonylation reaction rate.

6. The method of claim 1, wherein in the charging step, the metal-containing catalyst is present in an amount between about 200 and about 1200 ppm (about $2\times10^{-3}$ to about $13\times10^{-3}$ M).

7. The method of claim 1, wherein in the charging step, the metal-containing catalyst is present in an amount between about 400 to about 1000 ppm (about $4\times10^{-3}$ to about $10\times10^{-3}$ M).

8. The method of claim 1, wherein in the charging step, the metal-containing catalyst is selected from the group consisting of rhodium based catalysts, iridium based catalysts, palladium based catalysts, or mixtures thereof.

9. The method of claim 8, wherein the metal-containing catalyst comprises a rhodium based catalyst.

10. The method of claim 9, wherein the rhodium based catalyst comprises rhodium metal, rhodium salts, rhodium oxides, rhodium acetates, organo-rhodium compounds, coordination compounds of rhodium, or mixtures thereof.

11. The method of claim 10, wherein the rhodium based catalyst comprises a rhodium-containing compound selected from the group consisting of $RhCl_3$; $RhBr_3$; $RhI_3$; $RhCl_3.3H_2O$; $RhBr_3.3H_2O$; $RhI_3.3H_2O$; $Rh_2(CO)_4Cl_2$; $Rh_2(CO)_4Br_2$; $Rh_2(CO)_4I_2$; $Rh_2(CO)_8$; $Rh(CH_3CO_2)_2$; $Rh(CH_3CO_2)_3$; $Rh[(C_6H_5)_3P]_2(CO)I$; $Rh[(C_6H_5P)]_2(CO)Cl$; Rh metal; $Rh(NO_3)_3$; $Rh(SnCl_3)[(C_6H_5)_3P]_2$; $RhCl(CO)[(C_6H_5)_3As]_2$; $RhI(CO)[(C_6H_5)_3Sb]_2$; $[Y][Rh(CO)_2X_2]$, where X is $Cl^-$, $Br^-$ or $I^-$; and Y is a cation selected from the group consisting of positive ions from Group IA of the Periodic Table of Elements, such as H, Li, Na, K, or Y is a quaternary ion of N, As or P; $Rh[(C_6H_5)_3P]_2(CO)Br$; $Rh[(n-C_4H_9)_3P]_2(CO)Br$; $Rh[(n-C_4H_9)_3P]_2(CO)I$; $RhBr[(C_6H_5)_3P]_3$; $RhI[(C_6H_5)_3P]_3$; $RhCl[(C_6H_5)_3P]_3$; $RhCl[(C_6H_5)_3P]_3H_2$; $[(C_6H_5)_3P]_3Rh(CO)H$; $Rh_2O_3$; $[Rh(C_3H_4)_2Cl]_2$; $K_4Rh_2Cl_2(SnCl_2)_4$; $K_4Rh_2Br_2(SnBr_3)_4$; $[H][Rh(CO)_2I_2]$; $K_4Rh_2I_2(SnI_2)_4$, and the like and mixtures thereof.

12. The method of claim 11, wherein the rhodium based catalyst comprises a rhodium-containing compound selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H][Rh(CO)_2I_2]$ or mixtures thereof.

13. The method of claim 12, wherein the rhodium based catalyst comprises a rhodium-containing compound selected from the group consisting of $[H][Rh(CO)_2I_2]$, $Rh(CH_3CO_2)_2$, $Rh(CH_3CO_2)_3$ or mixtures or combinations thereof.

14. The method of claim 8, wherein the metal-containing catalyst comprises an iridium based catalyst.

15. The method of claim 14, wherein the iridium based catalyst comprises an iridium-containing compound selected from the group consisting of $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2]^-H^+$, $[Ir(CO)_2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, $Ir_2O_3$, $IrO_2$, $Ir(acac)(CO)_2$, $Ir(acac)_3$, $Ir(Ac)_3$, $[Ir_3O(OAc)_6(H_2O)_3][OAc]$, and $H_2[IrCl_6]$.

16. The method of claim 15, wherein an iridium-containing compound is selected from the group consisting of acetates, oxalates, acetoacetates, and mixtures thereof.

17. The method of claim 1, wherein in the charging step, the metal-containing catalyst comprises an iridium-based catalyst including a co-catalyst including metals and metal compounds selected from the group consisting of osmium, rhenium, ruthenium, cadmium, mercury, zinc, gallium, indium, and tungsten, their compounds, and mixtures thereof.

18. The method of claim 1, wherein in the charging step, the R group of the ROH or AcOR and RI is a linear alkyl group having between 1 and 6 carbon atoms.

* * * * *